United States Patent [19]

Piwnica-Worms

[11] Patent Number: 5,407,653
[45] Date of Patent: Apr. 18, 1995

[54] EVALUATION OF THE MULTIDRUG RESISTANCE PHENOTYPE

[75] Inventor: David R. Piwnica-Worms, Wellesley, Mass.

[73] Assignee: Brigham and Women's Hospital, Boston, Mass.

[21] Appl. No.: 719,714

[22] Filed: Jun. 26, 1991

[51] Int. Cl.$^6$ .......................... A61B 5/05; A61B 6/00; A61K 49/00; G01N 23/00
[52] U.S. Cl. .................................. 424/1.11; 424/1.61; 424/1.65; 424/1.81; 424/1.85; 424/1.89; 424/9; 436/56; 436/57; 128/653.1; 128/653.4; 128/654
[58] Field of Search ................ 424/1.1, 450, 572, 573, 424/1.65, 9, 7.1, 1.11, 1.61, 1.85, 1.81, 1.89; 436/56, 57; 128/653.1, 653.4, 654

[56] References Cited

U.S. PATENT DOCUMENTS

| | | | |
|---|---|---|---|
| 4,452,774 | 6/1984 | Jones et al. | 424/1.1 |
| 4,837,306 | 6/1989 | Ling et al. | 530/387 |
| 5,025,020 | 6/1991 | Van Dyke | 514/280 |
| 5,186,923 | 2/1993 | Piwnica-Worms | 424/9 |

OTHER PUBLICATIONS

Herweijer, et al., "A Rapid and Sensitive Flow Cytometric Assay for the Detection of MDR Cells in Human Cancer," *Invest New Drugs* 7:442, Abstract 374 (1989).
Higgins, C. F. et al. *Bioessays* 8:111 (1988).
Ames, G. F. *Ann. Rev. Biochem.* 55:397 (1986).
Higgins, C. F. et al. *J. Bioenerg. Biomembr.* 22:571 (1990).
Hyde, S. C. et al. *Nature* 346:362 (1990).
Higgins, C. F. et al. *Phil Trans R. Soc. Lond. B* 326:353 (1990).
Gottesman, M. M. et al. *J. Biol. Chem.* 263:12163 (1988).
Bradley, G. et al. *Biochim. Biophy. Acta.* 948:87 (1988).
Juranka, P. F. et al. *FASEB, J.* 3:2583 (1989).
Gros, P. et al. *Cell* 47:371 (1986).
Chen, C. et al. *Cell* 47:381 (1986).
Yoshimura, A. et al. *Cancer Lets.* 50:45 (1990).
Efferth, Th. et al. *Arzneim.-Forsch./Drug. Res.* 38:1771 (1988).
Herweijer, H. et al. *Invest. New. Drugs* 7:442 Abstract 374 (1989).
Konen, P. L. et al. *J. Histochem Cytochem* 37:1141 (1989).
Gerlach, J. H. et al. *Nature* 324:485 (1986).
Higgins, C. F. et al. *Nature* 323:448 (1986).
McGrath, J. P. et al. *Nature* 340:400 (1989).
Skovsgaard, T. et al. *Cancer Treat. Rev. 11 (Suppl A)*: 63 (1984).
Larsson, R. et al. *Int. J. Cancer* 46:67 (1990).

*Primary Examiner*—Richard D. Lovering
*Assistant Examiner*—Lara E. Chapman
*Attorney, Agent, or Firm*—Sterne, Kessler, Goldstein & Fox

[57] ABSTRACT

The present invention relates to methods for detecting the multidrug resistance phenotype in vivo and in vitro. The invention particularly relates to methods of diagnosing the multidrug resistance phenotype by imaging, particularly scintigraphic imaging, in solid tumors in vivo or in tumors and biopsies in vitro. The methods of the present invention allow the diagnosis of multidrug-resistant tumor and other multidrug-resistant phenotypes without invasive surgical methods.

19 Claims, 4 Drawing Sheets

EVALUATION OF THE MULTIDRUG RESISTANCE PHENOTYPE

Part of the work leading to this invention utilized U.S. Government funds. The U.S. Government has certain rights in this invention.

BACKGROUND OF THE INVENTION

1. Field of the Invention

The present invention relates to methods for detecting the multidrug resistance phenotype in vivo and in vitro. The invention particularly relates to methods of diagnosing the multidrug resistance phenotype by imaging, particularly scintigraphic imaging, in solid tumors in vivo or in tumors and biopsies in vitro. The methods of the present invention allow the diagnosis of multidrug-resistant tumors and other multidrug-resistant phenotypes without invasive surgical methods.

2. Description of the Background Art

A. ATP Binding Cassette Transport Proteins (Higgins, C. F. et al., *Bioessays* 8:11 (1988); Ames, G. F., *Ann. Rev. Bochem.* 55:397 (1986); Higgins, C. F. et al., *J. Bioenerg. Biomembr.* 22:571 (1990); Hyde, S. C. et al., *Nature* 396:362 (1990); Higgins, C. F. et al., *Phil. Trans. R. Soc. Lond. B* 326:353 (1990)).

A large number of cellular proteins bind ATP, many of which utilize the free energy of ATP hydrolysis to drive particular biological reactions. Several of these comprise a subfamily, the members of which share considerable sequence homology. The region of homology extends over 200 amino acids. In several of the proteins the conserved domain comprises nearly the entire polypeptide. In others the conserved domain is only one segment of a multi-domain protein. These proteins include the multidrug resistance P-glycoprotein, the product of the White locus of Drosophila, procaryotic proteins associated with membrane transport, cell division, nodulation and DNA repair, the STE-6 gene product that mediates export of yeast α-factor mating pheromone, pfMDR that is implicated in chloroquine resistance of the malarial parasite, and the product of the cystic fibrosis gene (CFTR).

There are two short amino acid sequence motifs which are present in most if not all nucleotide binding proteins. The subfamily of ATP binding proteins that are relevant to this invention are distinct from all other ATP binding proteins in that they share considerably more sequence identity than is simply required for nucleotide binding. Other ATP binding proteins may possess the consensus nucleotide binding motifs but otherwise share no significant sequence similarity. This implies that the subfamily of proteins shares common functions in addition to the ability to bind ATP. Many of the proteins of the subfamily and those which are best characterized, are components of an active transport system which mediates the transport of molecules across the cytoplasmic membrane. They are recognized in the art as ATP-binding cassette superfamily of transport proteins (Hyde, S., et al., *Nature* 346:362 (1990)).

Several nucleotide binding protein-dependent transfer systems have been characterized in procaryotes. Each system requires a substrate binding protein located in the periplasm that provides a primary receptor for transport. The system also contains two integral membrane proteins that transport substrates across the membrane. The system further contains two peripheral membrane proteins thought to be located on the inner surface of the cytoplasmic membrane. These peripheral membrane proteins are members of the subfamily of bacterial and eucaryotic ATP binding proteins relevant to this invention.

P-glycoprotein is a four-domain protein consisting of two hydrophobic domains and two ATP binding domains. Besides the conserved ATP binding domains, there is a great deal of similarity between P-glycoprotein and bacterial binding protein dependent transport systems. The organization of this protein is remarkably similar to that of bacterial transport systems. The two hydrophobic domains in P-glycoprotein are homologous to each other. The same is true for the two hydrophobic components of the binding protein system.

There are also a number of differences. First, the P-glycoprotein consists of four domains encoded as a single polypeptide, whereas in bacteria the equivalent domains are on separate polypeptides. Second, P-glycoprotein pumps drugs out of the cell whereas the binding protein dependent transport system mediates uptake. Third, protein dependent transport systems require a periplasmic component which serves as the initial substrate binding site and delivers substrate to the membrane component. However, as far as is known there is no equivalent component which interacts with the P-glycoprotein. Fourth, there is an important difference between P-glycoprotein and the bacterial transport systems in substrate specificity. The bacterial systems are relatively specific and there is a separate system for each substrate. In contrast, P-glycoprotein exhibits a very broad specificity, handling a range of apparently unrelated drugs. However, most of the differences may be trivial rather than fundamental mechanistic differences. It is not uncommon for functions carried out by separate polypeptide chains in procaryotes to be fused into a single multifunctional protein in eukaryotes. Further, a small change in the organization of a transport system could promote efflux rather than uptake. Finally, the periplasmic components of bacterial systems can be viewed as a specific adaptation to the fact that bacteria have a periplasm.

The similarity between P-glycoprotein and the bacterial active transport system may be relevant to the mechanisms of multidrug resistance in eucaryotic cells. All available evidence is compatible with the view that P-glycoprotein is a eucaryotic transport system. Most chemotherapeutic drugs are lipophilic and can enter the cells passively. In multidrug-resistant cells, the intracellular concentration of these drugs is reduced in an energy-dependent manner. The most reasonable explanation for these findings is that P-glycoprotein is an active transport system, pumping drugs out of the cell.

B. Multidrug Resistance

One problem facing the cell biologist and oncologist is the tendency of cultured cells and tumors in patients to exhibit simultaneous resistance to multiple chemically unrelated chemotherapeutic agents. Tissue culture cells can be selected for resistance to a variety of drugs such as colchicine, doxorubicin (Adriamycin), actinomycin D and vinblastine. Increasing the concentration of the selecting agent in multiple small single steps results in high levels of cross resistance to these agents as well as many other drugs including other anthracyclines, Vinca alkaloids and epipodophyllotoxins (Gottesman, M. M. et al., *J. Biol. Chem.* 263:12163 (1988)).

Resistance of malignant tumors to multiple chemotherapeutic agents is a major cause of treatment failure (Wittes et al., *Cancer Treat. Rep.* 70:105 (1986); Bradley, G. et al., *Biochim. Biophy. Acta* 948:87 (1988); Griswald, D. P. et al., *Cancer Treat. Rep.* 65(S2):51 (1981); Osteen, R. T. (ed.), *Cancer Manual,* (1990)). Tumors initially sensitive to cytotoxic agents often recur or become refractory to multiple chemotherapeutic drugs (Riordan et al., *Pharmacol. Ther.* 28:51 (1985); Gottesman et al., *Trends Pharmacol. Sci.* 9:54 (1988); Moscow et al., *J. Natl. Cancer Inst.* 80:14 (1988); Croop, J. M. et al., *J. Clin. Invest.* 81:1303 (1988)). Cells or tissues obtained from tumors and grown in the presence of a selecting cytotoxic drug can result in cross-resistance to other drugs in that class as well as other classes of drugs including anthracyclines, Vinca alkaloids, and epipodophyllotoxins (Riordan et al., *Pharmacol. Ther.* 28:51 (1985); Gottesman et al., *J. Biol. Chem.* 263:12163 (1988)). Thus, acquired resistance to a single drug results in simultaneous resistance to a diverse group of drugs that are structurally and functionally unrelated.

The characteristics of the multidrug resistance phenotype have been analyzed by studies on normal and tumor cell lines isolated for resistance to selected cytotoxic drugs. One major mechanism of multidrug resistance in mammalian cells involves the increased expression of the 170-kDa plasma membrane glycoprotein, P-glycoprotein (for review, Juranka et al., *FASEB J* 3:2583 (1989); Bradley, G. et al., *Biochem. Biophys. Acta* 948:87 (1988)). Transfection of cloned P-glycoprotein genes into drug-sensitive cell lines has confirmed that an increased expression of P-glycoprotein is sufficient to cause multidrug resistance in experimental systems (i.e., Gros, P. et al., *Nature* 323:728 (1986)).

The nucleotide sequence of multidrug resistance cDNA (Gros, P. et al., *Cell* 47:371–380 (1986); Chen, C. et al., *Cell* 47:381–389 (1986)) indicates that it encodes a polypeptide similar or identical to P-glycoprotein and that these are members of the highly conserved class of membrane proteins similar to bacterial transporters and involved in normal physiological transport processes.

The multidrug resistance P-glycoprotein may function normally to extrude as yet unknown physiological substrates out of cells by an energy-dependent process (Arceci, R. J. et al., *PNAS USA* 85:4350 (1988)) in normal tissues. The gene is amplified and consequently overexpressed in malignant tissues. It is thus believed that by transporting chemotherapeutic agents out of the cells, P-glycoprotein renders tumors resistant to chemotherapy.

C. Visual Assay of Multidrug Resistance

Multidrug resistance has been detected in vitro in single cell suspensions and in cell monolayers. Yoshimura et al., (*Cancer Letters* 50:45 (1990)) used the uptake of rhodamine dye to screen for agents that overcome multidrug resistance in a cell line ("reversing agents"). The dye is accumulated in multidrug-resistant cells at a lower rate than it is accumulated in non-resistant cells and thus multidrug-resistant cells can be distinguished from non-resistant cells by comparing intracellular dye levels.

In this study, the authors monitored dye levels in multidrug-resistant cells in the presence and absence of verapamil, a known chemosensitizer (reversing agent used in chemotherapy to facilitate the uptake of a chemotherapeutic drug in drug-resistant tumor cells), and found that the dye accumulated to normal levels when the multidrug resistance phenotype was reversed with verapamil. The dye was administered to cells in a confluent monolayer. The cells were then either washed, solubilized, and the dye detected with a fluorescence spectrometer, or scanned in microtitre wells with a fluorescence microplate reader.

Efferth et al. (*Arzneim-Forsch* 38:1771 (1988)) also developed an in vitro assay to detect the multidrug resistance phenotype. They compared the levels of rhodamine dye in a cell sample with the levels of dye found in a control sample of normal cells. The dye was detected by forming a single cell suspension, pipetting the suspension onto slides, administering the dye to the cells on the slide and detecting dye uptake of cells on the slide.

Herweijer et al. (*Invest New Drugs* 7:442 (1989)) used on-line flow cytometry to detect cells with the multidrug resistance phenotype in a single cell suspension. The uptake kinetics of a fluorescent drug were measured on line first in the absence and then in the presence of a reversing agent.

Konen et al. (*J. Histochem. Cytochem.* 37:1141 (1989)) assayed efflux activity of the multidrug resistance transport system using fluorescence microscopy to monitor the accumulation of drugs in single cultured cells that were transformed with multidrug resistance DNA. They showed that the efflux pathway was inhibited when the cells were incubated with verapamil.

D. Scintigraphic Imaging with Hexakis (R-isonitrile) Technetium Complexes

Hexakis (R-isonitrile) technetium (I) complexes (where R is alkyl, substituted alkyl, aryl, or substituted aryl) are a class of low valence technetium ($^{99}$mTc) coordination compounds empirically designed as clinical myocardial perfusion imaging agents (Jones, A. G. et al., *Int. J. Nucl. Med. Biol.* 11:225 (1984), Holman, B. L., et al., *J. Nucl. Med.* 25:1350 (1984), Holman, B. L., et al., ibid 28:13 (1987), Sporn, V., *Clin. Nucl. Med.* 13:77 (1988)). Conceived to be used in a manner similar to thallus chloride for the noninvasive evaluation of coronary artery disease, the compounds exploit the more favorable emission characteristics of $^{99}$mTc for applications in clinical imaging (Strauss, H. W., et al., *Radiology* 160:577 (1986), Deutsch, E., et al., *Science* 214:85 (1981)). Chemical analysis of these complexes with the ground state $^{99}$Tc isotope shows them to be monovalent cations with a central Tc(I) core octahedrally surrounded by six identical ligands coordinated through the isonitrile carbon. The terminal R groups, when bound to the technetium, encase the metal with a sphere of lipophilicity (Jones, A. G., et al., *Int. J. Nuc. Med. Biol.* 11:225 (1984), Mousa, S. A., et al., *J. Nuc. Med.* 28:1351 (1987)).

These complexes are sufficiently lipophilic to partition into and through the hydrophobic core of biological membranes, but also combine this property with a delocalized cationic charge which renders the compounds responsive to the plasma and mitochondrial transmembrane potentials. This combination of lipophilicity and delocalized charge produces an unusual property for these pharmaceuticals. Unlike tissue binding of many other pharmaceuticals that depend on highly specific binding sites (high affinity receptors), these pharmaceuticals have a non-specific uptake mechanism. However, tissue interaction is highly specific for those tissues with high plasma membrane potentials, high mitochondrial membrane potentials, high mitochondrial content, or combinations of the above.

Because uptake of these compounds by tissues is non-specific, any living cell (and potentially, any tissue type) can retain the compounds. A further advantage is that the compounds have been shown to be safe in humans as diagnostic pharmaceuticals while maintaining the unique combination of properties that allow them to respond to membrane potential. Conversely, other classes of lipophilic cations or fluorescent probes of membrane potential (e.g., rhodamine 123) have been shown to be toxic to cells and mitochondria (Bernel, et al., Science 218:1117 (1982), Emaus, R. K., et al., Biochim. Biophys. Acta 850:436 (1986), Gear, A. R. L., J. Biol. Chem. 249:3628 (1974)). These compounds have not been injected into humans.

SUMMARY OF THE INVENTION

The present invention is based on the unexpected discovery that the scintigraphic imaging agent, hexakis (2-methoxyisobutyl isonitrile) technetium-99m (I) (Tc-MIBI), is transported out of cells against a concentration gradient by P-glycoprotein, the product of the multidrug-resistance gene and a member of the family of ATP-binding cassette transport proteins. In cells over-expressing the multidrug resistance gene, net accumulation of Tc-MIBI is very low compared to the net accumulation in cells that do not overexpress the multidrug resistance gene.

This unexpected discovery combined with the history of the clinical use of Tc-MIBI as a whole body imaging agent with no toxic activity at imaging doses, provides a method to evaluate the multidrug resistance phenotype in living cells in vivo and in tissues in vitro. This evaluation is done by administering agents that are transported by the multidrug transport system and which are detectable in living cells despite the presence of biological tissue intervening between the detection device and the cells in their in situ location. Thus, cells in the living body or in a tissue mass are detectable in situ.

In preferred embodiments of the invention, living cells are imaged. Agents that are useful in imaging procedures are administered to a patient or a tissue specimen. Imaging procedures include, but are not limited to, magnetic resonance, superconducting quantum interference device (squid), positron emission tomography, and, in highly preferred embodiments, imaging is by planar scintigraphy or single photon emission computed tomography (SPECT).

The method is applicable as a rapid and simple assay of multidrug-resistant cells in vitro and, more importantly, as an assay in instances in which presently available assay methods are impractical or impossible. For example, in excised tissues, multidrug-resistant cells are detected without the need for tissue dispersion and growth that could change the in vivo phenotype. The method is especially valuable as an in vivo assay whereby multidrug resistance tissue is detected without the need for traumatic surgery. In a highly preferred embodiment of the invention, multidrug-resistant tumors are detected in cancer patients without the need for surgery.

In preferred methods of the present invention, the multidrug phenotype is detected with Tc-MIBI. At imaging doses, Tc-MIBI is without chemotoxic effects. In alternative embodiments, detection is with the broader range of technetium complexes, other non-toxic imaging agents, and other non-toxic markers that are transported by the multidrug resistance transport system and which can be detected despite the occurrence of biological tissue intervening between the cells and the imaging device.

Accordingly, the invention is directed to methods of detecting the multidrug resistance phenotype in an animal, tissues, or cells by administering an agent which is transported by the multidrug resistance transport system and which is detectable in living cells, at distances removed from the cells by the presence of intervening tissue.

The invention is particularly directed to methods of detecting the multidrug resistance phenotype in an animal, tissues, or cells by administering an imaging agent, especially a scintigraphic imaging agent, which is transported by the multidrug resistance transport system.

The invention is particularly directed to a method of assaying the multidrug resistance phenotype of solid tumors in vivo and in vitro by administering to patients, explanted tumor, or cells, an agent that is transported by the multidrug resistance transport system.

The invention is also directed to designing chemotherapy regimens by assaying the multidrug resistance phenotype in patients or their explanted tissue either prior to or during treatment.

In the assays of the present invention, the agent alone is administered to the subject (cells, tissue, or patient) and the incorporation of agent is measured. Thereafter, the agent is co-administered with a reversing agent and the incorporation of the agent is again measured. If the subject contains multidrug-resistant cells, these cells will accumulate less of the agent when the agent alone is administered than they will when the agent is administered with a reversing agent. Thus, when the two measurements are compared, greater intracellular accumulation of the agent in the presence of the reversing agent indicates the presence of multidrug-resistant cells.

The invention is also practiced with any of the family of ATP-binding transport proteins of which the multidrug resistance transport protein P-glycoprotein is a member.

DESCRIPTION OF THE PREFERRED EMBODIMENTS

The present invention is based on the discovery that the gamma emitter, Tc-MIBI, commonly used as an imaging agent for myocardial perfusion analysis, is transported out of cells by the multidrug resistance transport system. This agent, normally taken up by living cells, is actively excluded from living cells by the multidrug resistance system. Thus, when the multidrug resistance gene is overexpressed by a cell, the net accumulation of this agent is reduced compared to the levels accumulated by normal cells or cells to which have been co-administered the agent plus an agent that reverses the multidrug resistance phenotype (reversing agent). In the latter two instances, the net accumulation of the agent is higher and can be distinguished from that of multidrug-resistant cells.

Accordingly, the invention is directed to methods of detecting the multidrug resistance phenotype in an animal, tissues, or cells by administering to the animal, tissues, or cells, an agent which is transported by the multidrug resistance transport system and which is detectable in living cells, at distances removed, by the presence of intervening tissue, from the in situ location of the cells. The methods encompass measuring the intracellular accumulation of the agent in the animal, tissues, or cells, and comparing the measurement with the measurement obtained with a control that does not express the multidrug resistance phenotype.

In preferred methods of the present invention, the multidrug resistance phenotype is detected in an animal, tissues, or cells by administering to the animal, tissues, or cells, an imaging agent, particularly a scintigraphic imaging agent, which is transported by the multidrug resistance transport system. The methods then encompass imaging the animal, tissues, or cells, and comparing the image with the image obtained with a control that does not express the multidrug resistance phenotype.

In general, the invention embodies methods to assay the multidrug resistance phenotype in instances that previously required invasive in vivo surgical procedures or time-consuming in vitro outgrowth procedures. In the former instance the procedure involves trauma, often to patients already traumatized by prior treatment. In the latter instance, the phenotype of ex-planted cells, subject to the different selective pressures of tissue culture, and no longer subject to the in vivo selective pressures in the patient, would be subject to genotypic and phenotypic alteration that could confound diagnosis and treatment.

The present invention, therefore, embodies methods of detecting the multidrug resistance phenotype in tissues in vivo without the need for invasive procedures and in whole tissue in vitro.

In one preferred embodiment of the invention, the net cellular accumulation of the agent alone is compared with the net cellular accumulation of the agent when it is co-administered with an agent that reverses the multidrug resistance phenotype ("reversing agent"). In the presence of a reversing agent or other inhibitor, the agent is not excluded from cells, whereas in the absence of a reversing agent, relative exclusion of the agent occurs. Thus, in multidrug-resistant cells, the agent will be detected to a greater extent when administered with a reversing agent than the extent to which it is detected when administered alone. The agent is, therefore, useful as a marker for detecting the multidrug resistance phenotype.

In preferred embodiments of the invention, the agent is an imaging agent. The preferred imaging agent of the present invention is Tc-MIBI. The presence or absence of expression of the multidrug resistance phenotype is evaluated by scintigraphic imaging (either planar or SPECT) with Tc-MIBI before and after the administration of the reversing agent. The tissue significantly expressing the multidrug resistance phenotype shows little Tc-MIBI localization in the absence of the reversing agent but enhanced uptake of Tc-MIBI during infusion of the reversing agent. The tissue not expressing the multidrug resistance phenotype shows Tc-MIBI localization initially, but does not demonstrate reversing agent-induced enhancement of net uptake.

However, the imaging methods of the present invention encompass any non-toxic imaging agent that is transported by the multidrug resistance transport system. Alternative preferred imaging agents include, but are not limited to, other hexakis (R-isonitrile) technetium (I) complexes. Other embodiments encompass analogous complexes of paramagnetic and susceptibility metals such as lipophilic cation complexes of Mn, Fe, Gd, Dys for use in magnetic resonance imaging in vivo and in vitro and labelled positron-emitting ligands useful in positron emission tomography ("PET" scan). Alternative embodiments encompass other gamma-emitting labels such as rhenium, indium, iodine, and copper.

One preferred embodiment relates to the source of the Tc isotope. The specific activity of the Tc-MIBI complex synsthesized from $TcO_4^-$ obtained directly from commercial molybdenum/technetium generators, is extremely high. For example, in various embodiments disclosed herein, Tc-MIBI was generally synthesized at $1-6 \times 10^8$ Ci/mole. By comparison, $[^3H]$ TPP+, another lipophilic cation, is commonly supplied commercially at 5–100 Ci/mole. This provides an opportunity to decrease the molar concentration of cation accumulation by the biological preparation, yet remain within detectable limits. Since rhodamine 123 and TPP+ have been reported to have toxic effects on mitochondrial function at typical loading activities, the high specific activity and therefore low concentrations of Tc-MIBI required for biological experiments minimize toxic side effects during physiological experimentation and clinical imaging with the enhancement process.

Typical reversing agents include verapamil and quinidine. However, the invention can be practiced with any agent that reverses the multidrug resistance phenotype. Examples of alternative reversing agents include, but are not limited to vinblastine, vincristine, adriamycin, colchicine, daunomycin, dactinomycin, vanadate, cyclosporine and tetraphenylborate.

In one in vivo embodiment of the invention, a patient receives the detection agent in both the presence and absence of a reversing agent. The treatment is in either order. If the two drugs are first administered together, then following the detection process, the reversing agent is given sufficient time to leave the system before the administration of the agent alone. Following the treatments and detection, the measurements of accumulation of the agent in both cases are compared. Multidrug resistance tissue is detected in the presence of a reversing agent but not in its absence. Using this method, multidrug resistant tissue is located without invasive procedures.

One of the most formidable obstacles to successful chemotherapeutic treatment of tumors is the acquisition by tumors of the multidrug resistance phenotype. Presently, the acquisition of multidrug resistance is usually discovered when the patient no longer responds to the prescribed chemotherapeutic regimen.

In vivo evaluation of the multidrug resistance phenotype is highly desirable. If it is necessary to ascertain the presence of drug-resistant tumor cells in a cancer patient with solid tumors, either prior to or during treatment, doing so without surgery is much preferred. However, the location of an multidrug resistance tumor may not be known, so surgery would be complicated or precluded. Moreover, the presence of multiple metastases or of masses that impinge on an organ may preclude surgery as an alternative.

Whole body imaging in patients with tumors has previously demonstrated uptake of Tc-MIBI within mediastinal and pulmonary metastasis from thyroid cancer (Muller, S. T., et al., *J. Nucl. Med.* 28:562 (abstract) (1987)), untreated malignant lung lesions (Hassan, I. M. et al., *Clin. Nuci. Med.* 14:333 (1989) and known bronchial carcinomas (Muller, S. T. et al., *J. Nucl. Med.* 30:845 (abstract) (1989)).

Accordingly, in a highly preferred method of the present invention, multidrug-resistant tumors are detected in cancer patients without the need for surgery by administering to cancer patients an imaging agent of the present invention in the presence and absence of a reversing agent and comparing the images.

In alternative methods of the present invention, agents are not detected by imaging but by quantitative measurement of the intracellular accumulation (e.g., in a gamma counter or as by scanning radiograms by densitometry).

In a highly preferred embodiment of the methods of the present invention the imaging agent is Tc-MIBI. The presence or absence of expression of the multidrug resistance phenotype in tumors is evaluated non-invasively by the scintigraphic imaging with Tc-MIBI of cancer patients before and after the administration of a reversing agent. Those tumors significantly expressing the multidrug resistance phenotype will show little Tc-MIBI localization in the absence of the reversing agent but enhanced uptake of Tc-MIBI within the tumor or metastasis during infusion of the reversing agent. Those tumors not expressing the multidrug resistance P-glycoprotein should show Tc-MIBI localization initially, but should not demonstrate reversing agent-induced enhancement of net uptake. Tc-MIBI is a preferred imaging agent for whole tissue imaging. Alternative imaging agents include, but are not limited to the agents mentioned above. A highly preferred combination is Tc-MIBI as the imaging agent and verapamil, quinidine, or cyclosporine as the reversing agent. However, the invention can be practiced with any agent that reverses the multidrug resistance phenotype. Examples of alternative reversing agents are discussed above.

The methods of the present invention are also applicable to whole tissue and cells in vitro. The invention is advantageous over current methods of determining the multidrug resistance phenotype in vitro because it is rapid and simple. Using presently available methods, before the multidrug resistance phenotype can be evaluated in whole tissue, a single cell suspension must be created (e.g., for flow cytometry) or even more laborious techniques must be used, such as monolayer cell culture. Using the method of the current invention, it is possible to detect the multidrug resistance phenotype in tissue without, or with minimum, disaggregation. Thus, therapeutic regimens may be decided with less delay than with presently available methods.

Current in vitro procedures for detecting the multidrug resistance phenotype involve forming either cell monolayers or single cell suspensions because the detectable emission (i.e., beta rays or fluorescence) does not penetrate and pass through intervening biological material. Thus, there is no rapid procedure for assaying the multidrug resistance phenotype of cells in a tissue or a cell mass, such as a tumor or tumor biopsy. Tissue would have to be dispersed into single cells for analysis and may have to be cultured. Cell culture, however is time consuming and also alters the selection pressures so that the cultured cells do not display the same phenotype or genotype as the cells in vivo. For example, the overexpression of the multidrug resistance gene in a tumor occurs as a result of the selection and multiplication of single or a few mutant cells as the tumor is subjected to a chemotherapeutic drug. If the tumor is excised and grown in tissue culture, the genotype may change because the selection pressure is not the same. This may interfere with the proper analysis of the tumor and hence with prescription of a effective therapeutic regimen. With the methods of the present invention, however, the tumor could be analyzed without dispersion and growth in culture. Relevant prescription would then be more likely.

Further, tumors are usually genotypically and phenotypically heterogeneous. New genotypes may arise in a very small or minute portions of a tumor and may not be detectable by routine methods. For example, the multidrug resistance phenotype occurring in a small area of a tumor, may be missed if the tumor cells are dispersed or merely biopsied. With the methods of the present invention, since a small area would be intact, imaging the tumor would reveal such small pockets of multidrug resistant cells.

Accordingly, the invention embodies methods of assaying the multidrug resistance phenotype in whole tissue or tissue biopsies by incubating the tissue or biopsy with the agents of the present invention. In a preferred embodiment, the tissue is exposed to the agent in the presence and absence of a reversing agent, such as those mentioned above. Accumulation of the agent in the tissue is measured in both cases and the measurements are compared. In alternative embodiments, the agent is administered alone and the measurement obtained is compared with the measurement obtained with normal control tissue. In one preferred embodiment, the agent is an imaging agent. Tc-MIBI is a preferred imaging agent for whole tissue imaging. Alternative imaging agents include, but are not limited to the agents mentioned above. A highly preferred combination is Tc-MIBI as the imaging agent and verapamil or quinidine as the reversing agent.

The invention also embodies methods of designing chemotherapy regimens by assaying the multidrug resistance phenotype in patients or their explanted tissue either prior to or during treatment. During the course of chemotherapy, when it is determined that a multidrug resistance-negative tumor (previously showing agent localization) converts or recurs with multidrug resistance (expressed as loss of agent localization), this valuable information is used to guide therapeutic management of the patients. Accordingly, in an embodiment of the invention, patients are evaluated for the multidrug resistance phenotype prior to initiation or continuation of chemotherapy. Those patients deemed phenotypically multidrug resistance-positive are spared the toxic and debilitating side effects of futile chemotherapy and alternative regiments or treatment ought.

With the method of the present invention, it is also possible to evaluate in vivo the efficacy of alternative chemotherapeutic drugs. In one embodiment of the invention, the ability of a drug to act as a chemosensitizer (reversing agent used in chemotherapy to facilitate the uptake of a chemotherapeutic drug in drug-resistant tumor cells) is determined. An agent of the present invention and a potential chemosensitizer are administered to a patient. If the drug is able to reverse the multidrug resistance phenotype, the agent will be retained in the patient's tumor cells in the presence of that drug but not in its absence. The chemosensitizer is then used to facilitate the administration of or to test the efficacy of anti-tumor drugs.

Further, the location of tumors not detectable by standard means (e.g., CAT scan) is determinable if these tumors have the multidrug resistance phenotype. Thus, the methods of the present invention provide means to monitor progression or regression of the disease during chemotherapy.

The discovery of the present invention also provides embodiments in which agents are transported by other members of the ATP binding cassette transport family of proteins. For example, one embodiment of the invention is a test for sensitivity to new anti-malarial agents in drug-resistant malaria parasites in which the pfMDR gene is over-expressed or a test of bacterial transport function where the transporter belongs to the family.

By the terms "ATP-binding cassette transport protein" is intended, for the purpose of the present invention, a protein that is a member of the ATP-binding cassette superfamily of transport proteins. This family is recognized by sequence identity over a "cassette" of about 200 amino acids. This cassette is an ATP-binding domain which is the distinguishing feature of this family of transport proteins. These domains share about 30–40% sequence identity among the members of the superfamily. A putative member of the superfamily would be recognized by sequence comparison of the primary structure with a primary consensus sequence or individual sequences of these proteins using routine computerized sequence scanning methods. The degree of identity in the conserved domain between any pair of these proteins is essentially the same whichever two proteins are compared. It is important to emphasize that these ATP-binding proteins are distinct from other proteins that bind ATP in that the sequence homology is much greater than is required for merely nucleotide binding. That is, the homology extends considerably beyond the two consensus nucleotide-binding sequences of Walker et al. (EMBO J. 1:945 (1982)) which comprise five and nine amino acids.

The ordinary skilled artisan would recognize a putative member of this distinctive family by computerized alignment of the primary sequence with the primary sequence of one or more of the known ATP-binding cassette transport proteins. Computerized sequence comparison and alignment is done with any one of the well-known and routinely used sequence homology/identity scanning programs. These programs would be readily available to the skilled artisan. The putative member of the family should contain, in addition to the two short consensus nucleotide-binding sequences of Walker et al. (EMBO J. 1:945 (1982) incorporated herein by reference), a region of homology surrounding the consensus sequences wherein the region of homology spans around 200 nucleotides and is approximately 30–40% homologous with a region in the known members of the family. To ensure identity, the skilled artisan would generally know to compare the novel sequence with several known members of the family (see, for example, Juranka et al. *FASEB J.* 3:2584 (1989); Gerlach et al. *Nature* 324:485 (1986); Chen et al. *Cell* 47: 381 (1986); Gros et al. *Cell* 47:371 (1986); Higgins et al. *BioEssays* 8:111 (1988); Kamijo et al. *J. Biol. Chem.* 265:4534 (1990); Higgins et al. *Nature* 323:448 (1986); Hyde et al. *Nature* 396:362 (1990) all herein incorporated by reference).

By the term "cell" is intended any one of the components that make up an organized tissue, consisting of a nucleus which is surrounded by cytoplasm which contains the various organelles and is enclosed in the cell or plasma membrane. For the purpose of the present invention, cells are in vivo as part of the living organism, in explanted tissue taken from a living organism, or in cell culture.

By the term "multidrug resistance" for the purpose of the present invention is intended the phenotype that occurs in a cell as the result of the overexpression of the gene product of the multidrug resistance gene or its homologues. By "multidrug resistance gene" is intended that DNA sequence which encodes P-glycoprotein and its functional equivalents and whose amplification confers upon a cell cross-resistance to toxic drugs. By "homologue" is intended the DNA sequence in another species, which sequence corresponds to the multidrug resistance gene.

By the term "administer" is intended any method for introducing the compositions of the present invention into a subject. Typical methods include, but are not limited to, oral, intranasal, parenteral (intravenous, intramuscular, or subcutaneous), or rectal. The term "administer" also relates to the application of substance ex vivo as in cell or organ culture.

By "compound" is intended a chemical entity, whether in the solid, liquid, or gaseous phase, which entity may be used on or administered to animals, including humans, as an aid in the diagnosis, treatment, or prevention of disease or other abnormal condition, for the relief of pain or suffering, or to control or improve any physiologic or pathologic condition. The term "compound" should be read to include synthetic compounds, natural products and macromolecular entities such as polypeptides, polynucleotides, or lipids and also small entities such as neurotransmitters, ligands, hormones or elemental compounds. The term "compound" is meant to refer to that compound whether it is in a crude mixture or purified and isolated.

By the term "transport" for the purpose of the present invention is intended the ATP-binding protein-dependent movement of a compound across the membrane of a living cell.

By "intervening" is intended, for the purpose of the present invention, the occurrence of biological tissue between the cell being detected and the detection device. The biological tissue of relevance is of a thickness such that it cannot be traversed by beta emission, fluorescence, or other clinical detection means such as heat (thermography) or spectrophotometry. Therefore, such means of detection are not useful for detection of multi-drug-resistant cells or tissue in vivo, where the organs and other biological tissue in a living body interfere with or prevent detection. These means, similarly, are not useful for detecting multidrug-resistant cells enclosed in a cell mass such as a tissue biopsy or whole tumor.

By the term "imaging" for the purpose of the invention is intended the production in clarity, contrast, and detail in images, either by analogue or digital devices, especially in radiological images.

By the term "scintigraphy" is intended the production of two dimensional or three dimensional reconstructed images of the distribution of radioactivity in tissues after the internal administration of radionuclide, the images being obtained by a scintillation camera.

By the term "coadminister" is intended that each of at least two components be administered during a time frame wherein the respective periods of biological activity overlap. Thus the term includes sequential as well as coextensive administration of the compounds of the present invention.

By the terms "chemosensitizer" or "reversing agent" are intended for the purpose of the present invention, a compound that allows the net accumulation of toxic compounds in multidrug-resistant cells equivalent to the net accumulation of said toxic compounds in non-multidrug-resistant cells.

By the term "tumor" is intended for the purpose of the present invention, a new growth of tissue in which the multiplication of cells is uncontrolled and progressive. The tumor that is particularly relevant to the invention is the malignant tumor, one in which the primary tumor has the properties of invasion and metastasis and which shows a greater degree of anaplasia than do benign tumors.

By "R" is intended alkyl, substituted alkyl, aryl, or substituted aryl groups. R groups are found in the general formula —$CR_3$ where R can be identical or different and includes the elements H, C, N, O, S, F, Cl, Br, and I. Representative examples include, but are not limited to, —$CH_3$, —$CH_2CH_3$, CH ($CH_3$)$_2$, —C($CH_3$)$_3$, —C($CH_3$)$_2$ O$CH_3$, —C($CH_3$)$_2$ COO$CH_3$, —C ($CH_3$)$_2$ OCO$CH_3$ —C($CH_3$)CON$H_2$, —$C_6H_5$, —$CH_2(C_6H_4$-4)OH, or any of their isomeric forms having the general composition as the isonitrile radionuclide complexes in U.S. Pat. No. 4,452,774 which is incorporated herein by reference.

By "alkyl" is intended any straight, branched, saturated, unsaturated or cyclic $C_{1-20}$ alkyl group. Typical $C_{1-20}$ alkyl groups include, but are not limited to, methyl, ethyl, n-propyl, i-propyl, n-butyl, t-butyl, i-butyl, pentyl and hexyl groups.

By "aryl" is intended any cyclic hydrocarbon based on a six-membered ring. Typical aryl groups include, but are not limited to, phenyl, naphthyl, phenanthryl, and anthracyl groups.

By "substituted alkyl" and "substituted aryl" is intended any alkyl or aryl group in which at least one carbon atom is covalently bonded to any functional group comprising the atoms H, C, N, O, S, F, Cl, Br and I.

Typical substituted alkyl groups include but are not limited to amino, $C_{1-6}$ alkylamino, $C_{2-12}$ dialkylamino, $C_{1-6}$ alkoxy, and $C_{2-6}$ alkylcarboxy. Typical substituted aryl groups include, but are not limited to the above-listed aryl groups substituted by halo, hydroxy, $C_1$–$C_6$ alkoxy, amino, and the like.

By the term "animal" is intended any living creature that contains cells in which the intramembrane potential is reduced by the administration of agents of this invention. Foremost among such animals are humans; however, the invention is not intended to be so-limiting, it being within the contemplation of the present invention to apply the compositions of the invention to any and all animals which may experience the benefits of the application.

By the term "over-express" is intended for the purpose of the present invention, the production of an ATP-binding cassette transport protein in a cell type in amounts exceeding that normally produced in that cell type. Although expression may vary amongst normal cell types, within each type an ATP-binding cassette transport protein is expressed within a normal physiological range. Over-expression may be due to gene amplification, an increase in RNA transcription rates, increase in RNA stability, increase in mRNA translation, or any other molecular process which results in amounts of ATP-binding cassette transport protein exceeding those amounts found in normal cells. The normal range of expression in a given cell type can be determined by routine methods as by assaying the ATP-binding cassette transport protein, its mRNA, or its gene. Assays may be those commonly used in the art such as immunoassay, PAGE, western blot, Southern and northern blots, Cot analysis, Rot analysis, and competition hybridization procedures.

Having now generally described the invention, the following examples illustrate the methods of the present invention.

EXAMPLES

EXAMPLE 1

Experimental Solutions

Control buffer was a modified Earle's balanced salt solution (MEBSS) with the following composition (nM): $Na^+$, 145; $K^+$, 5.4; $Ca^3$, 1.2; $Mg^{2+}$, 0.8; Cl, 152; $H_2PO_4$, 0.8; $SO_4^{2-}$, 0.8; dextrose, 5.6; HEPES, 4.0; and bovine calf serum, 1% (v/v); pH 7.4±0.05; 37° C. Verapamil and quinidine were dissolved into DMSO prior to addition to buffer. DMSO alone has no significant effect on contractile activity, action potential configuration (Lieberman, M., et al., *Dev. Biol.* 31:380–403 (1973)) or Tc-MIBI uptake kinetics (Piwnica-Worms, D., et al., *Circ.* 82:1826–1838 (1990)).

Synthesis of the radiolabeled compound [$^{99m}$Tc]MIBI was performed using a one-step kit developed at DuPont Medical Products, Billerica, Mass. The kit reaction vial contains the isonitrile ligand in the form of tetrakis (2-methoxy isobutyl isonitrile) Copper (I) tetrafluoroborate (1.0 mg), a stannous chloride reducing agent (0.075 mg L-cysteine hydrochloride (1.0 mg), Sodium Citrate (2.6 mg) and mannitol (20 mg). The intrinsically radiolabelled complex was formed by adding [$^{99}$MTc]TcO$_4^-$ (20–30 mCi, 2-25 pmol/mCi) in 1–2 ml saline (0.15M, NaCl), obtained from a commercial molybdenum/technetium generator (DuPont Medical Products, Billerica, Mass.), to the kit reaction vial, heating at 100° C. for 15 min, and allowing to cool to room temperature producing an almost quantitative yield of the [$^{99m}$Tc](MIBI)$_6^+$ complex. Excess reducing agent and starting materials were separated from the radiolabelled component as follows: the contents of the reaction vial were loaded via syringe onto a reversed phase Sep-Pak cartridge (C-18, Waters Assoc., Milford, Mass.) pre-wet with ethanol (3 ml, 90%) followed by distilled water (5 ml). Hydrophilic impurities were eluted from the cartridge by washing with saline (10 ml, 0.15M) and the desired Tc-MIBI collected by elution with ethanol/saline (2 ml; 9:1, v:v). Final total $^{99m}$Tc activity in the 2 ml effluent (stock) was assayed in a standard dose calibrator (CRC-12, Capintec, Ramsey, N.J.). Radiochemical purity was found to be greater than 97% by thin layer chromatography (aluminum oxide plates) using ethanol (absolute) as the mobile phase.

Statistics

Values are presented as mean±SEM. Statistical significance was determined by the two-tailed unpaired Student's t test where indicated in the text (Wallenstein, S., et al., Circ. Res. 47:1–9 (1980)).

EXAMPLE 2

Tissue Culture of LZ and V79 Cells

LZ and V79 cells were grown to confluence in approximately four days on 25 mm glass cover slips placed on the bottom of 100 mm plastic culture dishes in Minimal Essential Media (MEM) Alpha Medium supplemented with 10% fetal calf serum, 1% L-glutamine, and 1% penicillin/streptomycin solution at 37° C. in a 5% $CO_2$/95% air humidified environment. Serial passage was performed by gently shaking the cells off the culture dish during exposure to 0.25% trypsin solution for 2-3 minutes (room temperature) and diluting the cell suspension in growth medium 1:4 for LZ cells and 1:20–40 for V79 cells. For LZ cells, growth medium was also supplemented with 4 μg/ml adriamycin.

EXAMPLE 3

Radiotracer Uptake Methods

Radioactive uptake methods have been described in detail (Pinwnica-Worms, D., et al., Circ. 82:1826=1838 (1990)). Briefly, coverslips with confluent cells were removed from culture media and pre-equilibrated for 40–60 seconds in MEBSS buffer. Uptake and retention experiments were initiated by immersion of coverslips in 60 mm glass Pyrex dishes containing loading solution consisting of buffer with 0.1–0.6 nM [$^{99m}$Tc-MIBI] (0.01–0.4 Ci/nmole; 25–100 uCi/ml). Preparations were removed at various times and rinsed three times in separate 25 ml volumes of ice-cold (2° C.) isotope-free buffer for 8 seconds each to clear extracellular spaces. For washout experiments, preparations were incubated in loading solution for 15 minutes, rinsed as above in ice-cold buffer, and then immersed in 30 ml of isotope-free MEBSS (37° C.) for the times indicated. Cell-associated activity was then determined. Preparations and aliquots of the loading buffer and stock solutions were counted in a well-type sodium iodide gamma counter after which cell protein on each coverslip was extracted in 1% sodium dodecylsulfate with 10 mM sodium borate and assayed by the method of Lowry (Lowry, O. H., et al., J. Biol. Chem. 193:265-275 (1951)). Tc-MIBI binding to glass coverslips without cells was used as an estimate of non-specific adhesion to the substrate (<% of total activity obtained with cellular preparations); this value was subtracted from total uptake determinations to derive the cell-associated counts. Use of generator equilibrium equations (Lamson, M. L., et al., J. Nucl. Med. 16:639–641 (1975)) allowed calculation of absolute moles of Tc-MIBI in solutions and preparations. Results were therefore expressed as fmol cellular Tc-MIBI/mg protein per nM extracellular Tc-MIBI concentration.

EXAMPLE 4

Figure 1:
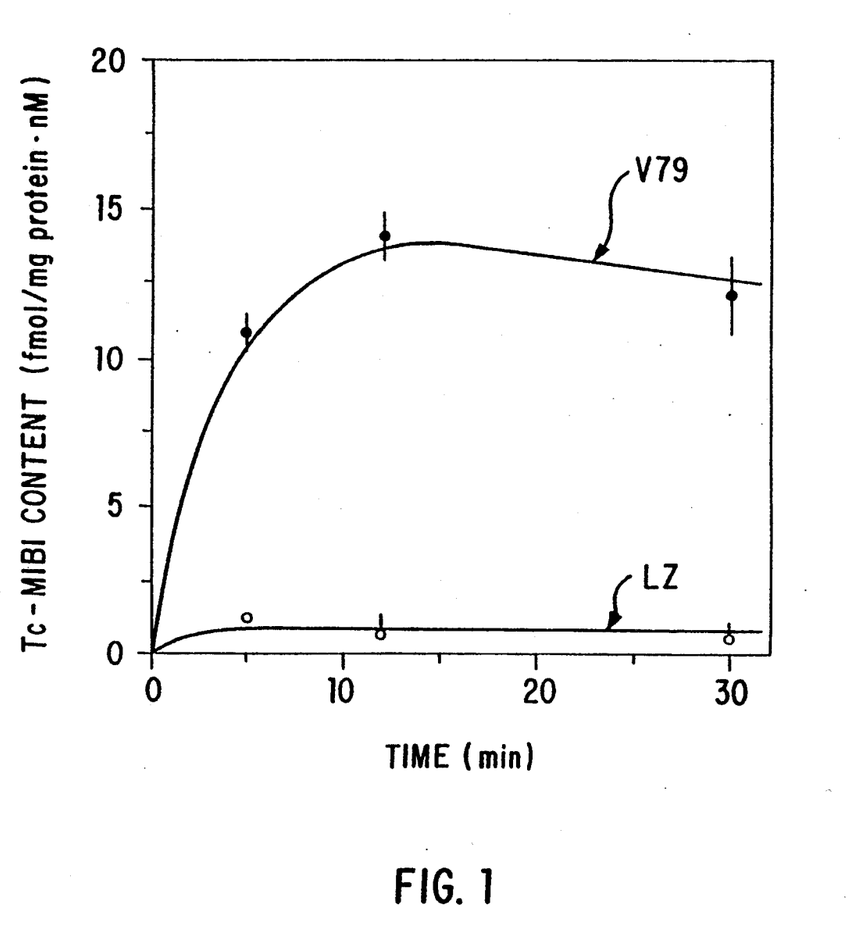
FIG. 1. Accumulation of Tc-MIBI in LZ cells (highly expressing multidrug resistance) (0) and V79 cells (modestly expressing multidrug resistance) (●). Cells were incubated in modified Earle's balanced salt solution (MEBSS) containing Tc-MIBI (53 uCi/ml; 20.7 pmol/mCi) for various times and cell associated activity determined as described previously (Chiu et al., J. Nucl. Med. 31:1646–1653 (1990)). Results are expressed as fmol cellular Tc-MIBI/mg protein per nmolar extracellular Tc-MIBI. Points represent the mean±SEM of three determinations each.

Net accumulation of Tc-MIBI in LZ cells, a cell line highly selected for multidrug resistance phenotype, is only 0.3 fmoles Tc-MIBI/mg protein per nmolar extracellular Tc-MIBI (FIG. 1). This value is lower than that expected by simple equilibration of the agent into the cytosolic water space (approx. 5 fmoles/mg protein per $nM_o$) and implies active extrusion of Tc-MIBI by the multidrug resistance P-glycoprotein. High inhibitory doses of verapamil (1 mM) increases net accumulation of Tc-MIBI greater than 100-fold over net uptake in the absence of the inhibitor. V79 cells, a cell line which modestly expresses multidrug resistance P-glycoprotein, demonstrates control accumulation of Tc-MIBI to plateau levels 20-fold higher than LZ cells (FIG. 1). This is consistent with expectations for a cellular phenotype with a less robust efflux pathway for Tc-MIBI.

EXAMPLE 5

Figure 2:
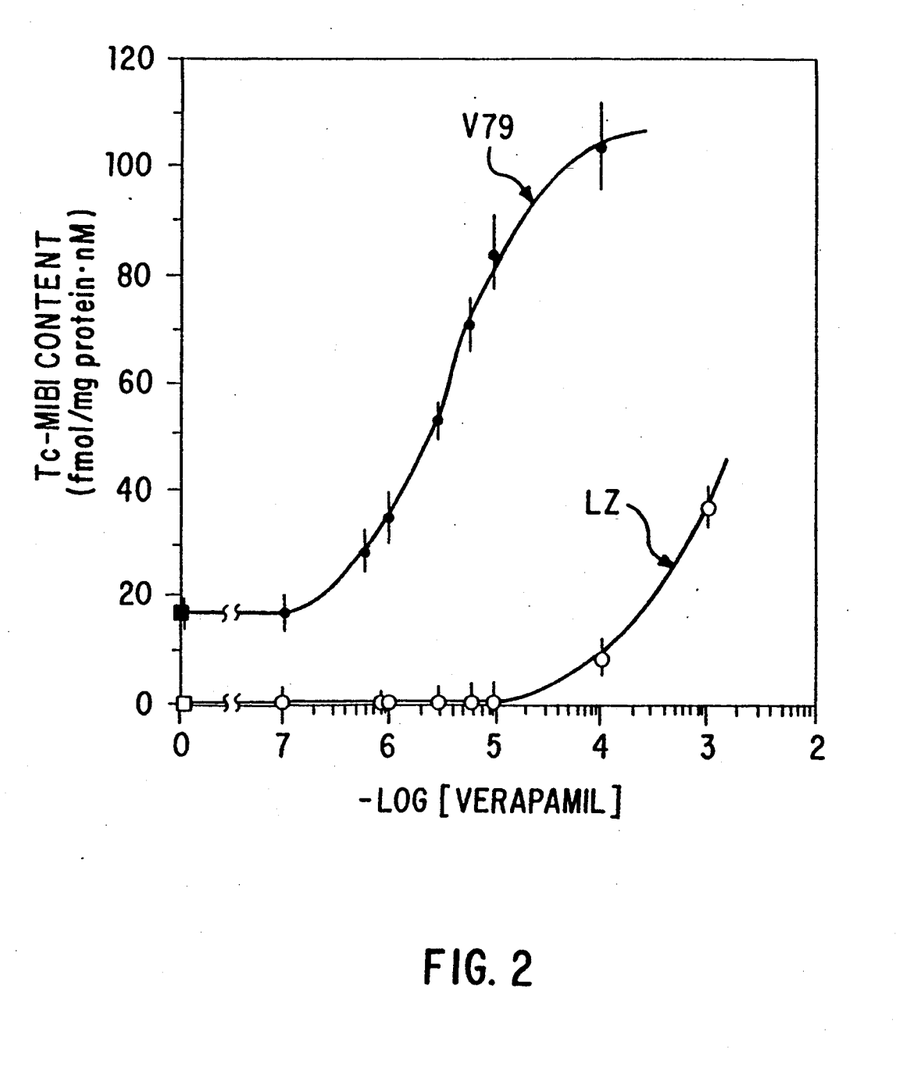
FIG. 2. Concentration-effect curve for verapamil enhancement of Tc-MIBI accumulation in LZ (□, O) and V79(■, ●) cells. Preparations were incubated for 15 minutes in MEBSS containing Tc-MIBI in the absence (□, ■) or presence (O, ●) of verapamil at the indicated concentrations and then cell associated activity determined. Points represent the mean±SEM of 3–4 determinations each.

Verapamil, a known inhibitor of multidrug resistance P-glycoprotein (Gottesman, M. M. et al., J. Biol. Chem. 263:12163 (1990)), increases net accumulation of Tc-MIBI in LZ cells to the higher levels expected for potential dependent uptake of the agent (FIG. 2). Verapamil also enhances the net accumulation of Tc-MIBI in V79 cells causing an 6-fold increase in net Tc-MIBI accumulation (FIG. 2).

EXAMPLE 6

Figure 3:
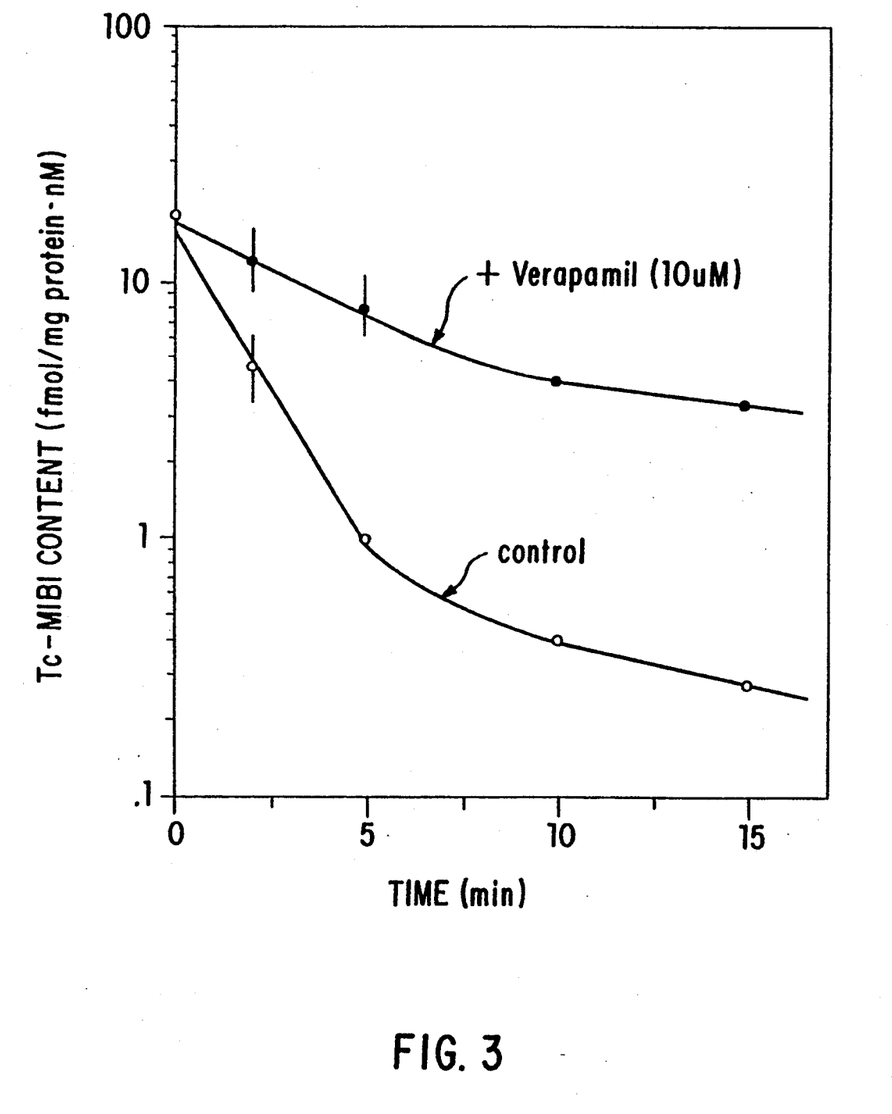
FIG. 3. Inhibition of Tc-MIBI efflux from V79 cells by verapamil. Cells were incubated in MEBSS containing Tc-MIBI for 15 minutes (plateau loading), then transferred to Tc-MIBI-free MEBSS washout buffer for various times in the absence (O) or presence (●) or verapamil (10 μm). Cell associated tracer activity was determined and expressed as fmol cellular Tc-MIBI/mg protein per nmolar Tc-MIBI concentration in the uptake buffer. Each point represents the mean of 4 determinations. Error bars represent±SEM when larger than symbol. Note semilog plot.

Verapamil (10 uM) is shown to directly inhibit unidirectional efflux of Tc-MIBI from V79 cells (FIG. 3).

EXAMPLE 7

Figure 4:
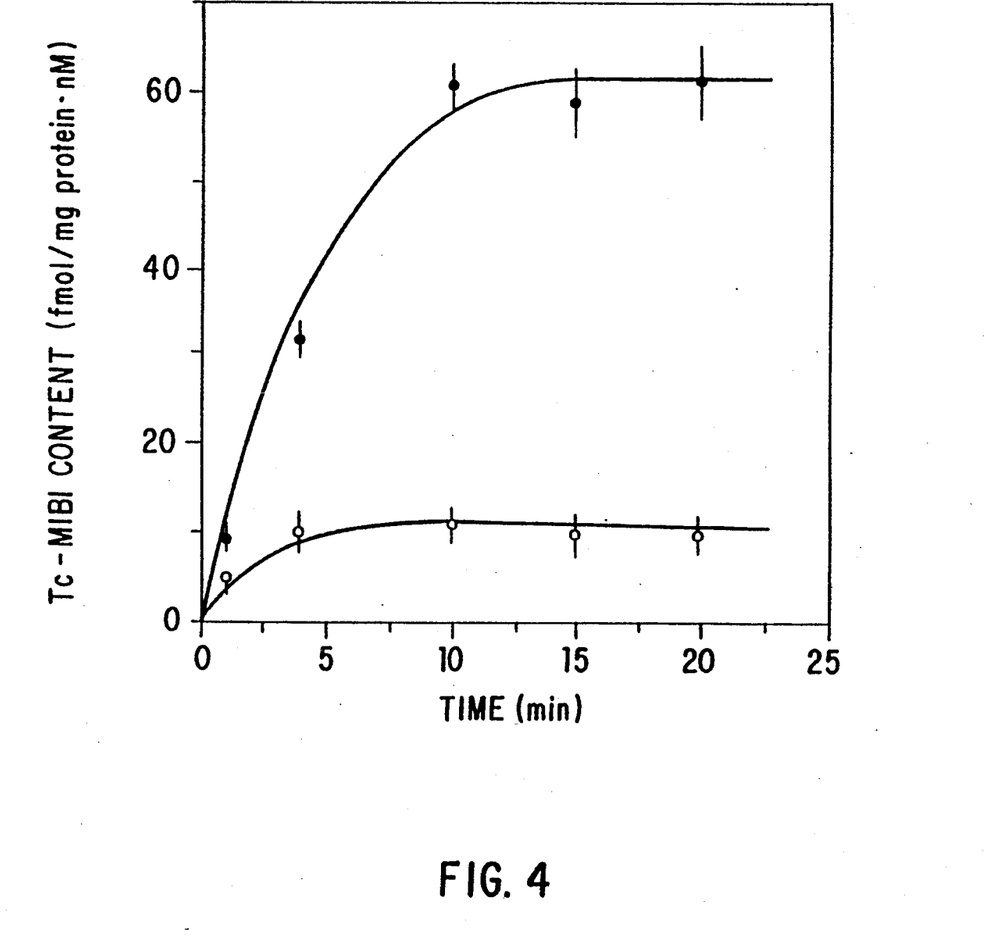
FIG. 4. Effect of quinidine on accumulation of Tc-MIBI in V79 cells. Cells were incubated for various times in MEBSS containing Tc-MIBI in the absence (O) presence (●) of quinidine (10 uM) and then cell associated activity determined. Points represent the mean±SEM of three determinants each.

Quinidine, another drug known to inhibit the multidrug resistance P-glycoprotein, also increase net accumulation of Tc-MIBI in V79 cells (FIG. 4).

What is new and claimed and intended to be covered by a letters patent of the United States is:

1. A method of detecting a living cell having the multidrug resistance phenotype comprising:
(a) administering to said cell having the multidrug resistance phenotype an imaging effective amount of a compound which is transported in across the membrane of said cell by the protein product of the multidrug resistance gene;
(b) detecting said compound in said cell in the presence of biological tissue intervening between said cell and the device by which said compound is detected; and
(c) comparing the amount of compound detected in step (b) with the amount of compound in a cell that does not have the multidrug resistance phenotype; and wherein said compound is labeled such that the compound is detectable in the presence of biological tissue intervening between said cell and the device by which said compound is detected.

2. A method of imaging a living cell having the multidrug resistance phenotype comprising:
   (a) administering to said cell having the multidrug resistance phenotype an imaging effective amount of a compound which is transported in across the membrane of said cell by the protein product of the multidrug resistance gene;
   (b) imaging said cell in the presence of biological tissue intervening between said cell and the device by which said compound is detected; and
   (c) comparing the image in step (b) with the image in of a cell that does not have the multidrug resistance phenotype;
   and wherein said compound is labeled such that the compound is detectable in the presence of biological tissue intervening between said cell and the device by which said compound is detected.

3. The method of claim 2 wherein said imaging is by scintigraphy.

4. A method of detecting a living cell having the multidrug resistance phenotype comprising:
   (a) administering to said cell having the multidrug resistance phenotype an imaging effective amount of a non-toxic compound which is transported in across the membrane of said cell by the protein product of the multidrug resistance gene;
   (b) detecting said compound in said cell in the presence of biological tissue intervening between said cell and the device by which said compound is detected;
   (c) co-administering to said cell an imaging effective amount of the compound of step (a) and a chemosensitizer;
   (d) detecting said compound in said cell in the presence of biological tissue intervening between said cell and the device by which said compound is detected; and
   (e) comparing the amount of said compound detected in step (b) with the amount of compound detected in step (d);
   and wherein said compound is labeled such that the compound is detectable in the presence of biological tissue intervening between said cell and the device by which said compound is detected.

5. A method of imaging a living cell having the multidrug resistance phenotype comprising:
   (a) administering to said cell having the multidrug resistance phenotype an imaging effective amount of a non-toxic compound which is transported in across the membrane of said cell by the protein product of the multidrug resistance gene;
   (b) imaging said cell in the presence of biological tissue intervening between said cell and the device by which said compound is detected;
   (c) co-administering to said cell an imaging effective amount of the compound of step (a) and a chemosensitizer;
   (d) imaging said cell in the presence of biological tissue intervening between said cell and the device by which said compound is detected; and
   (e) comparing the image in step (b) with the image in step (d);
   and wherein said compound is labeled such that the compound is detectable in the presence of biological tissue intervening between said cell and the device by which said compound is detected.

6. The method of claim 5 wherein said imaging is by scintigraphy.

7. The method of any one of claims 1–6 wherein said cell is in vivo.

8. The method of any one of claims 1–6 wherein said cell is in vitro.

9. The method of claim 7 wherein said cell is a tumor cell.

10. The method of claim 8 wherein said cell is a tumor cell.

11. The method of either of claims 3 or 6 wherein said compound is hexakis (R-isonitrile) technetium wherein R is alkyl, substituted alkyl, aryl or substituted aryl.

12. The method of claim 11 wherein said compound is hexakis (methoxyisobutylisonitrile) technetium (I).

13. A method of locating a tumor in situ having the multidrug resistance phenotype comprising:
   (a) administering to an animal with said tumor having the multidrug resistance phenotype an imaging effective amount of a compound which is transported across the membrane of a cell in said tumor by the protein product of the multidrug resistance gene;
   (b) detecting said compound in said animal in the presence of biological tissue intervening between said cell and the device by which said compound is detected; and
   (c) comparing the amount of compound detected in step (b) with the amount of compound in a cell that does not have the multidrug resistance phenotype;
   and wherein said compound is labeled such that the compound is detectable in the presence of biological tissue intervening between said cell and the device by which said compound is detected.

14. A method of locating a tumor having the multidrug resistance phenotype comprising:
   (a) administering to an animal with said tumor having the multidrug resistance phenotype an imaging effective amount of a compound which is transported across the membrane of a cell in said tumor by the protein product of the multidrug resistance gene;
   (b) imaging said animal in the presence of biological tissue intervening between said cell and the device by which said compound is detected; and
   (c) comparing the image in step (b) with the image of a cell that does not have the multidrug resistance phenotype;
   and wherein said compound is labeled such that the compound is detectable in the presence of biological tissue intervening between said cell and the device by which said compound is detected.

15. The method of claim 14 wherein said imaging is by scintigraphy.

16. A method of locating a tumor in situ having the multidrug resistance phenotype comprising:
   (a) administering to an animal with said tumor having the multidrug resistance phenotype an imaging effective amount of a non-toxic compound which is transported across the membrane of a cell in said tumor by the protein product of the multidrug resistance gene;
   (b) detecting said compound in said animal in the presence of biological tissue intervening between said cell and the device by which said compound is detected;

(c) co-administering to said animal an imaging effective amount of the compound of step (a) and a chemosensitizer;

(d) detecting said compound in said animal in the presence of biological tissue intervening between said cell and the device by which said compound is detected; and (e) comparing the amount of said compound detected in step (b) with the amount of compound detected in step (d);

and wherein said compound is labeled such that the compound is detectable in the presence of biological tissue intervening between said cell and the device by which said compound is detected.

17. A method of locating a tumor in situ having the multidrug resistance phenotype comprising:

(a) administering to an animal with said tumor having the multidrug resistance phenotype an imaging effective amount of a non-toxic compound which is transported across the membrane of a cell in said tumor by the protein product of the multidrug resistance gene;

(b) imaging said animal in the presence of biological tissue intervening between said cell and the device by which said compound is detected;

(c) co-administering to said animal an imaging effective amount of the compound of step (a) and a chemosensitizer;

(d) imaging said animal in the presence of biological tissue intervening between said cell and the device by which said compound is detected; and (e) comparing the image in step (b) with the image in step (d);

and wherein said compound is labeled such that the compound is detectable in the presence of biological tissue intervening between said cell and the device by which said compound is detected.

18. The method of claim 17 wherein said imaging is by scintigraphy.

19. A method of detecting a living cell wherein said cell overexpresses an ATP-binding cassette transport protein, said method comprising: (a) administering to said cell over-expressing an ATP-binding cassette transport protein an imaging effective amount of a compound which is transported in across the membrane of said cell by said ATP-binding cassette transport protein;

(b) detecting said compound in said cell in the presence of biological tissue intervening between said cell and the device by which said compound is detected; and (c) comparing the amount of compound detected in step (b) with the amount of compound in a cell that does not over-express said ATP-binding cassette transport protein.;.

and wherein said compound is labeled such that the compound is detectable in the presence of biological tissue intervening between said cell and the device by which said compound is detected.

* * * * *